(12) United States Patent
Henning

(10) Patent No.: US 8,712,503 B2
(45) Date of Patent: Apr. 29, 2014

(54) PELVIC REGISTRATION DEVICE FOR MEDICAL NAVIGATION

(75) Inventor: Stefan Henning, Schwaben (DE)

(73) Assignee: Brainlab AG, Feldkirchen (DE)

( * ) Notice: Subject to any disclaimer, the term of this patent is extended or adjusted under 35 U.S.C. 154(b) by 1717 days.

(21) Appl. No.: 11/857,465

(22) Filed: Sep. 19, 2007

(65) Prior Publication Data

US 2008/0077004 A1    Mar. 27, 2008

Related U.S. Application Data

(60) Provisional application No. 60/827,277, filed on Sep. 28, 2006.

(30) Foreign Application Priority Data

Sep. 21, 2006 (EP) ..................................... 06019755

(51) Int. Cl.
*A61B 5/05* (2006.01)

(52) U.S. Cl.
USPC .............................. 600/429; 600/427; 606/1

(58) Field of Classification Search
USPC ...................... 600/427, 429; 606/1
See application file for complete search history.

(56) References Cited

U.S. PATENT DOCUMENTS

| 4,341,220 | A | 7/1982 | Perry |
| 4,624,245 | A | 11/1986 | Mullin et al. |
| 5,249,581 | A | 10/1993 | Horbal et al. |
| 5,327,907 | A | 7/1994 | Fischer |
| 5,681,326 | A | 10/1997 | Lax |
| 6,143,003 | A | 11/2000 | Cosman |
| 6,351,662 | B1 * | 2/2002 | Franck et al. ................. 600/429 |
| 6,499,488 | B1 | 12/2002 | Hunter et al. |
| 6,925,339 | B2 | 8/2005 | Grimm et al. |
| 2003/0153829 | A1 | 8/2003 | Sarin et al. |
| 2004/0102792 | A1 | 5/2004 | Sarin et al. |
| 2004/0267284 | A1 * | 12/2004 | Parmer et al. ................. 606/130 |
| 2005/0075632 | A1 | 4/2005 | Russell et al. |
| 2006/0084889 | A1 | 4/2006 | Drumm et al. |

FOREIGN PATENT DOCUMENTS

| CH | 240449 | 12/1945 |
| DE | 634127 | 8/1936 |
| EP | 1 632 193 | 3/2006 |
| WO | 01/21084 | 3/2001 |

* cited by examiner

*Primary Examiner* — Long V. Le
*Assistant Examiner* — Nicholas Evoy
(74) *Attorney, Agent, or Firm* — Tucker Ellis LLP

(57) ABSTRACT

A device for registering in a medical navigation system a position and/or orientation of a patient's pelvis includes a pelvic registration frame. A plurality of positioning elements are arranged on the pelvic registration frame so as to define a plane, wherein the plurality of positioning elements are movable with respect to each other to enable placement of the positioning elements at defined pelvic points of the patient's pelvis. At least one position transmitter is arranged in an unambiguously defined position and/or orientation relative to the frame.

15 Claims, 3 Drawing Sheets

PELVIC REGISTRATION DEVICE FOR MEDICAL NAVIGATION

RELATED APPLICATION DATA

This application claims priority of U.S. Provisional Application No. 60/827,277 filed on Sep. 28, 2006, which is incorporated herein by reference in its entirety.

FIELD OF THE INVENTION

The invention relates to medical navigation and, more particularly, to a device and method for registering a position and/or orientation of a patient's pelvis in conjunction with medical navigation.

BACKGROUND OF THE INVENTION

In order to provide navigational assistance (image-assisted surgery) during a medical procedure, such as a procedure involving the pelvis, the spatial position of the pelvis is ascertained. It is of particular interest to ascertain how specific anatomical pelvic planes lie in a space defined by a coordinate system of a medical tracking system (which may be assigned to a medical navigation system). Planes of interest include, for example, the frontal pelvic plane, which is defined by the two iliac spines and the two pubic spines, and/or the mid-sagittal pelvic plane.

EP 1 632 193 A1 describes a hip registration system comprising a registration frame provided with reflective markers. When using such a registration frame, a sufficient number of markers should be detected in a free line of sight by the tracking cameras of the tracking system.

US 2003/0153829 A1 discloses a navigation system for pelvic operations in which a patient positioning frame is used. A reference array is attached to the frame, wherein the frame, based on the reference array, can be registered using a pointer instrument.

SUMMARY OF THE INVENTION

A device for registering a position and/or orientation of a patient's pelvis for medical navigation comprises a pelvic registration frame bearing positioning elements that can be placed at defined pelvic points. The device or part thereof (e.g., the frame) is assigned at least one position transmitter that is or can be arranged in an unambiguously definable position and/or orientation relative to the frame.

A spatial orientation of the frame and/or the defined orientation of the position transmitter (or number of position transmitters) can be assigned to one or more anatomical pelvic planes, e.g., to the mid-sagittal plane or the frontal pelvic plane. Preferably, the at least one position transmitter already lies in such a specific parallel plane and/or is defined in it's orientation to a parallel plane.

The position transmitter can be an electromagnetic sensor, in particular a magnetic tracking coil, the position and/or orientation of which can be detected by a magnetic medical tracking system. It is possible to provide a number of electromagnetic sensors or magnetic tracking coils and/or to include such sensors or coils integral with the device. The at least one electromagnetic sensor or and/or the at least one magnetic tracking coil can be attached to the frame in a fixed orientation.

It should be noted that the term "position transmitter" need not necessarily designate a sensor or marker; this could theoretically also be the magnetic field generator. It is also conceivable for the magnetic field generator to be attached to a patient positioner in a defined arrangement, while the sensor is fastened in the pelvic bone.

The frame can comprise at least one positioning and/or orientation aid, in particular a recess, for a sensor carrier that can bear an electromagnetic sensor or magnetic tracking coil. The orientation aid or recess then can serve to arrange the sensor carrier so as to determine its direction and/or position. In other words, the sensor carrier can only be positioned by means of the orientation aid in a particular and predefined position or orientation to the frame such that the orientation of the frame also can be determined from the position of the sensor carrier and/or sensor (coil) contained therein.

It is also possible, either alone or in combination with the above embodiments, for a number of position transmitters to be designed as x-ray markers and arranged on the frame, wherein the markers consist of a material that is impermeable to x-ray radiation. Further, the frame can substantially consist of a material that is permeable to x-ray radiation, at least in the vicinity of the markers. This enables the registration frame and/or its x-ray markers to be imaged in an x-ray image (e.g., fluoroscopic image), and it is likewise possible to deduce, from the imaged marker positions, the spatial position of the registration frame and therefore also the position of the pelvis.

The x-ray markers can be arranged on the frame as attachments or inserts. It is also possible to design the frame and the x-ray markers such that the x-ray markers form or replace a part of the frame contour, such as an edge portion or corner portion of the frame.

Additionally, it is also conceivable, for example, to detect a patient and/or the frame using a pre-operative or intra-operative CT scanner (wherein x-rays are also used). The frame may be identified in two-dimensional fluoroscopic images (if fluoroscopy is used), or in two-dimensional tomographic images and/or a three-dimensional data set in the case of CT. Thus, wherever fluoroscopic registration is mentioned herein, CT-based registration, in principle, also can be used.

The device also can be used to register one or more anatomical landmarks (e.g., the pubic point and the iliac spine also referred to as ASIS (Anterior Superior Iliac Spine) point). Additionally, the method steps or methods that are performed when using the device to register the pelvis also are described herein. Registration can be performed in one step, including registration of patients lying in a lateral position. In contrast to conventional methods and systems, for example those in accordance with EP 1 632 193 A1, when using the device and method described herein it is no longer necessary for the patient to be registered lying on his back and then moved to a lateral position. This time and effort, and any possible sterility problems, can in particular be avoided using the device and method provided herein, since they are no longer based on a tracking technology that is dependent on a stationary line of sight between the tracking cameras and optical markers. Furthermore, electromagnetic, fluoroscopic or CT-based registration can save time compared to conventional fluoroscopic registration or marker registration, since only one step and/or fewer fluoroscopic images are needed.

If electromagnetic sensors, such as magnetic tracking coils, are used as the position transmitters, they can be arranged differently on the mechanical frame device so as to determine the orientation of the pelvic planes. As mentioned, one advantage is that the magnetic sensors need not be constantly visible to a camera system and can be used to measure the required plane and direction information for any conceivable patient position. This is in particular advantageous when navigation methods are already being used that are based solely on magnetic tracking.

A single magnetic sensor is in principle sufficient to determine and record the direction of the pelvic planes. Depending on the position of the planes and a suitable structure of the registration frame and/or a suitable arrangement of the magnetic sensor, the position of a plane also could be directly determined by the position of the sensor. In this case, it is merely necessary to ensure that the sensor and its arrangement in the frame already corresponds to such a pelvic plane orientation.

On the one hand, the electromagnetic sensors or magnetic tracking coils, which provide five-dimensional or six-dimensional position and direction information, can be rigidly and/or fixedly arranged on the frame. In another embodiment, an electromagnetic sensor can be provided on a carrier, wherein the carrier may be shaped as a small pin. This pin then can be arranged in an unambiguous position relative to the frame by means of an orientation aid.

Additionally or alternatively, the position of the pelvic planes can be registered using a C-arm fluoroscopy apparatus. In this embodiment, the registration frame, which may be permeable to x-ray radiation, would comprise implemented metal markers or metal marker edges. The markers also can be made of another material that absorbs or is impermeable to x-ray radiation.

Software then can automatically detect the position of the markers of the respective frame and/or of the corners or edges configured as markers. From this information, the position of the planes can be deduced by calculation. The registered pelvic planes can be positionally stored in relation to a pelvic reference array, an electromagnetic sensor on the pelvis or an electromagnetic sensor on the frame. Additional fluoroscopic recordings of the ASIS or pubic points would not be necessary in order to register the pelvic planes. The patient could be positioned in a lateral position while the fluoroscopic recordings are produced. Another advantage is the improved visibility of the frame markers or corner markers of a pelvic registration frame relative to the anatomical pelvic landmarks. Automatically detecting the markers/corners in a fluoroscopic image would work more reliably, since the markers in the frame are more clearly identifiable in the image (clearer contrast) than for example bone parts that are surrounded by soft tissue and/or do not exhibit any clear bone edges.

BRIEF DESCRIPTION OF THE DRAWINGS

The forgoing and other features of the invention are hereinafter discussed with reference to the drawing.

DETAILED DESCRIPTION

Figure 1:
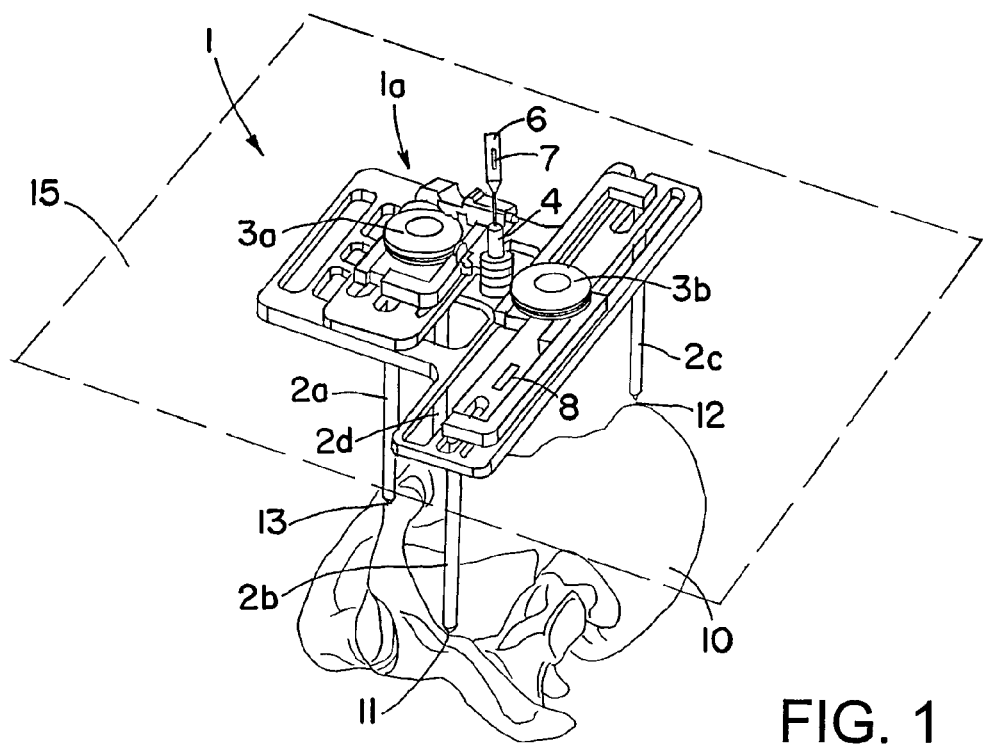
FIG. 1 illustrates an exemplary pelvic registration frame in accordance with the present invention, wherein the frame is shown positioned on the pelvis.

FIG. 1 shows an exemplary pelvic registration device 1 comprising a frame 1a from which rod-shaped positioning elements 2a, 2b, 2c and 2d project in a downward direction perpendicular to a plane 15 of the frame. Adjusting means 3a and 3b allow the positioning elements 2a and 2d, and 2b and 2c respectively, to be moved towards or away from each other so as to adapt the device to a patient-specific anatomy. A plane formed by the tips of the positioning elements 2a-2d or by the frame 1 is not changed by the width adjustment made via adjusting elements 3a and 3b.

With the aid of the osseous pelvis 10, also shown in FIG. 1, it is possible to show how the registration frame 1a for registering the pelvic planes is placed onto specific landmarks. Here, the specific landmarks are the two frontal iliac spines 11 and 12 on which the tips of the positioning elements 2b and 2c come to rest, and the two pubic spines, only one of which is visible and indicated as 13. The tips of the positioning elements 2a and 2d come to rest on the two pubic spines. When the registration frame 1a is placed on the osseous pelvis 10 in this way, the position of its elements is in a defined relationship to the spatial pelvic position and in particular to the anatomical pelvic planes. In the present example, a flat part of the frame 1a lies parallel to a plane that is indicated as the frontal pelvic plane. A plane that lies perpendicular to the frontal pelvic plane and halfway between each of the elements 2b and 2c and the elements 2a and 2d is the mid-sagittal plane of the pelvis 10. FIG. 1 also schematically shows an electromagnetic sensor 8, which in the present example is a magnetic tracking coil, the orientation and position of which can be determined (in six dimensions or degrees of freedom) within a magnetic tracking system that comprises a magnetic field generator (not shown).

FIG. 1 also shows an alternative or additional embodiment for a magnetic tracking position transmitter, configured as a pin 6 and comprising an electromagnetic sensor 7 (magnetic tracking coil 7). The pin 6 is shown above a rod-like extension 4, which in the present case is perpendicular on the plane 15 defined by the surface of the frame 1a.

If an electromagnetic sensor 8 is used that is rigidly attached to or in the frame 1a, then its position relative to the upper plane 15 of the frame 1a is known, and it is then possible to deduce the orientation of the plane 15 of the frame 1a and therefore also the orientation of the frontal pelvic plane directly from the direction information obtained from the sensor 8. If only the position of these planes need be known for navigational assistance, then it is accordingly sufficient to merely locate such a magnetic sensor 8 connected to the frame 1a and to know the frame geometry.

Figure 2:
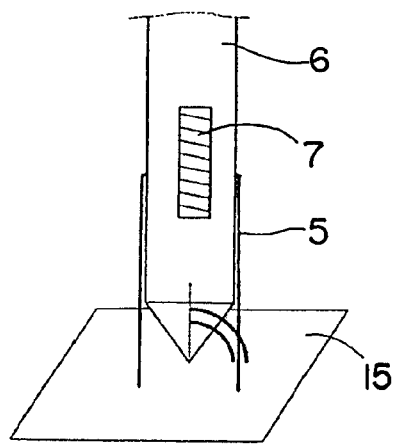
FIG. 2 is a schematic diagram of an exemplary pin comprising an electromagnetic sensor (e.g., a magnetic tracking coil) inserted into an orientation aid in accordance with the invention and shown in relation to a pelvic plane.

Another option is to place an electromagnetic sensor 7 on a carrier, e.g., pin 6. This carrier or pin 6 can be attached to or inserted into the frame 1a in a defined position relative to the frame 1a. In the present example, this is achieved using the rod-like continuation or extension 4 that is perpendicular to the plane 15 of the frame 1a, and one possible position is schematically shown in FIG. 2. In FIG. 2, the pin 6 comprising the electromagnetic sensor 7, which in this case is arranged axially and attached in a defined location in the pin 6, is inserted into a hollow portion 5 of the extension 4. The orientation of the pin 6 and also the orientation of the sensor 7 is therefore defined; it is perpendicular on the plane of the frame 1a indicated as 15 in FIG. 2. If the design is advantageously embodied, said plane 15 of the frame 1 is also simultaneously parallel to the frontal pelvic plane. The orientation of the plane 15 of the frame 1a can be determined from the perpendicular relationship between the magnetic sensor 7 and the plane 15 of the frame 1a; its position then also can be calculated from the lengths of the positioning elements 2a to 2d, the height of the frame 1a and the height of the extension 4, and from the distance between the sensor 7 and the tip of the pin 6.

In a preferred embodiment, when the frame 1a is lying on the four anatomical points, the plane 15 of the frame 1a will be parallel to the pelvic plane. The sensors 7 or 8 can lie in a defined direction with respect to this plane (i.e., known to the software), but need not necessarily be attached to the frame so as to be perpendicular to the plane 15. However, it is also conceivable that the frame 1a need not be parallel to the pelvic plane, as long as the actual orientation has been previously defined and is known to the software (by calibrating or by predefined programming), e.g., the pin or pins 6 could, for ergonomic reasons, be obliquely attached to the frame 1a.

The sensor 7 would then be calibrated in such a way that the position and orientation of the sensor coordinate system is in a fixed relation to the pin 6. The pin 6 could thus also be regarded as a pointer device, the position and orientation of which can be tracked (in six dimensions or degrees of freedom). It is also possible to define positions and directions of planes in a fixed relation to the pin. A first plane theoretically could be positioned perpendicular to the symmetrical pin axis. Another plane could be positioned coaxially with respect to the axis and perpendicular to the first plane. The orientation and/or receiving mechanism for the pin 6 on the pelvic registration frame 1a can be designed in such a way that the pin 6 can only be arranged in a defined orientation to the four previously described anatomical landmarks, i.e., the ASIS or pubic points. The pin 6 is therefore always orientated in a defined way to the anatomical frontal pelvic plane, and can indicate a direction and position of the frontal pelvic plane and the mid-sagittal plane. The pin 6 could of course also be analogously arranged at different positions on the frame 1a and in a defined relation to anatomical pelvic landmarks, in order to determine the orientations of other planes or axes.

Figure 3:
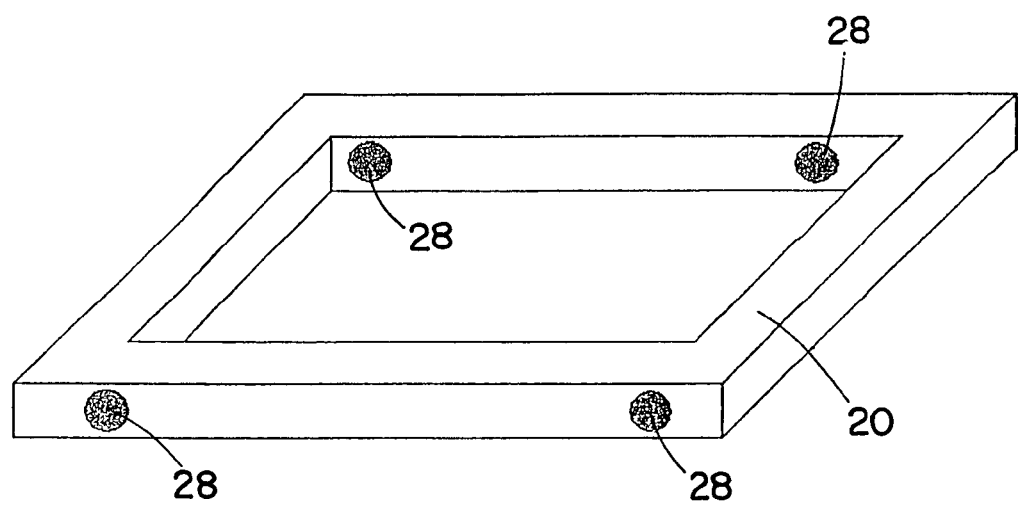
FIG. 3 is a schematic representation of another exemplary registration frame in accordance with the invention comprising metal markers for fluoroscopic registration.

As already indicated above, a pelvic registration frame 1a such as that shown in FIG. 1, for example, can be spatially determined by fluoroscopic registration. FIG. 3 schematically illustrates another exemplary frame 20 that includes four x-ray markers 28 fastened thereto in different locations. For clarity, positioning elements 2a-2d and adjusting elements 3a and 3b have been omitted. If the markers 28 are attached to the frame 20 at fixed positions in relation to the pelvic landmarks, it is then possible to automatically detect these x-ray positive markers 28 in a frame 20 that is permeable to x-ray radiation. When the frame is placed on the patient's pelvis, as described above, the markers 28 have a fixed position relative to the pelvis and relative to the pelvic planes. The design and dimensions of the frame 20 and the positions of the markers 28 can be implemented in a navigation computer program. The number of markers 28 is not fixedly defined. It is for example possible to provide only a single marker, which is correspondingly designed and identifies its position in the x-ray or CT image by its shape.

The pelvic registration frame 20 and a pelvic sensor (optical reference array or electromagnetic sensor) can be placed on the patient's pelvis, before x-ray images or fluoroscopic images are produced. If a C-arm fluoroscopy apparatus is used, a calibration kit can be attached to the C-arm. Once the images have been produced, together with the pelvic registration frame 20 placed on the patient, the navigation computer program can automatically ascertain the position of the markers 28, while the frame 20 is not visible due to its radiolucency. The position of the markers 28 or frame 20 in relation to the pelvic sensor or pelvic reference array can be stored. The system can thus ascertain the directions of the anatomical pelvic planes (frontal pelvic plane, mid-sagittal plane) in relation to the pelvic sensor or reference array.

Figure 4:
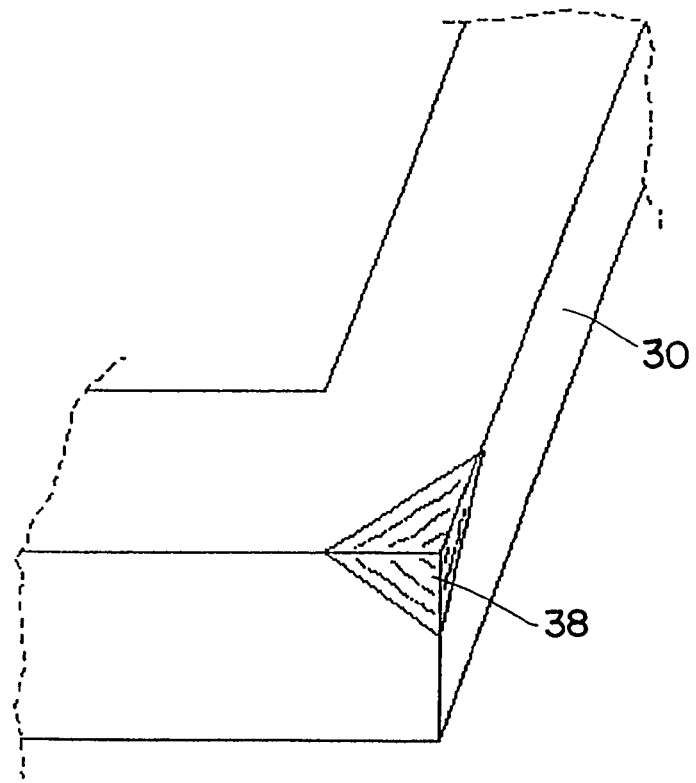
FIG. 4 is a schematic representation of corner portion of yet another exemplary frame in accordance with the invention, wherein the frame includes a corner marker.

Instead of adding the x-ray markers to the frame, the markers can be configured as parts of the frame 20. FIG. 4 shows how a corner of a frame 30 is replaced with an x-ray positive material, which then forms an x-ray marker 38. The position of the planes would then similarly be ascertained using a number of such x-ray markers 38, as described above for the separate markers 28. Alone or in combination with the above-described frame, the edges of the frames 20 and 30 may also detected. If the edges are in a defined and fixed relation to the pelvic contact points, the software can use an edge detecting algorithm to determine the position of the frames 20 and 30. For this purpose, at least the edges of the frames 20 and 30 are impermeable to x-rays.

It should again be noted that the frames 20 and 30 shown in FIGS. 3 and 4 are merely schematic representations. Attaching x-ray markers as shown in these figures can of course also be applied to a frame such as is for example shown in FIG. 1.

Pelvic registration, by means of fluoroscopic registration of the pelvic registration frame, may proceed as follows: the frame is first placed onto the pelvis (as shown in FIG. 1), and a pelvic sensor (e.g., a trackable device such as an optical or electromagnetic sensor for a corresponding tracking system) is then attached to the pelvis. The fluoroscopic images are then produced, wherein a fluoroscopic registration kit can be used, and the position of the pelvic sensor is stored. The navigation software then can automatically detect the frame markers in the fluoroscopic or x-ray images, and the position of the markers or frame can be calculated in relation to the pelvic sensor so as to determine one or more pelvic planes of the patient.

Using the information obtained above, it is possible to show the direction of the anatomical pelvic planes, ascertained from the orientation of the frame, in a coordinate system defined by the pelvic sensor.

Other steps can optionally also be performed, such as, for example acquiring pelvic landmark points (for example, ASIS or pubic points) using a pointer device or by automatically detecting said points in the obtained images. The position of the calculated pelvic planes in relation to an acquired pelvic landmark also can be ascertained and displayed, and it is also possible to virtually display the pelvic planes in relation to previously recorded image data using an image display device.

Figure 5:
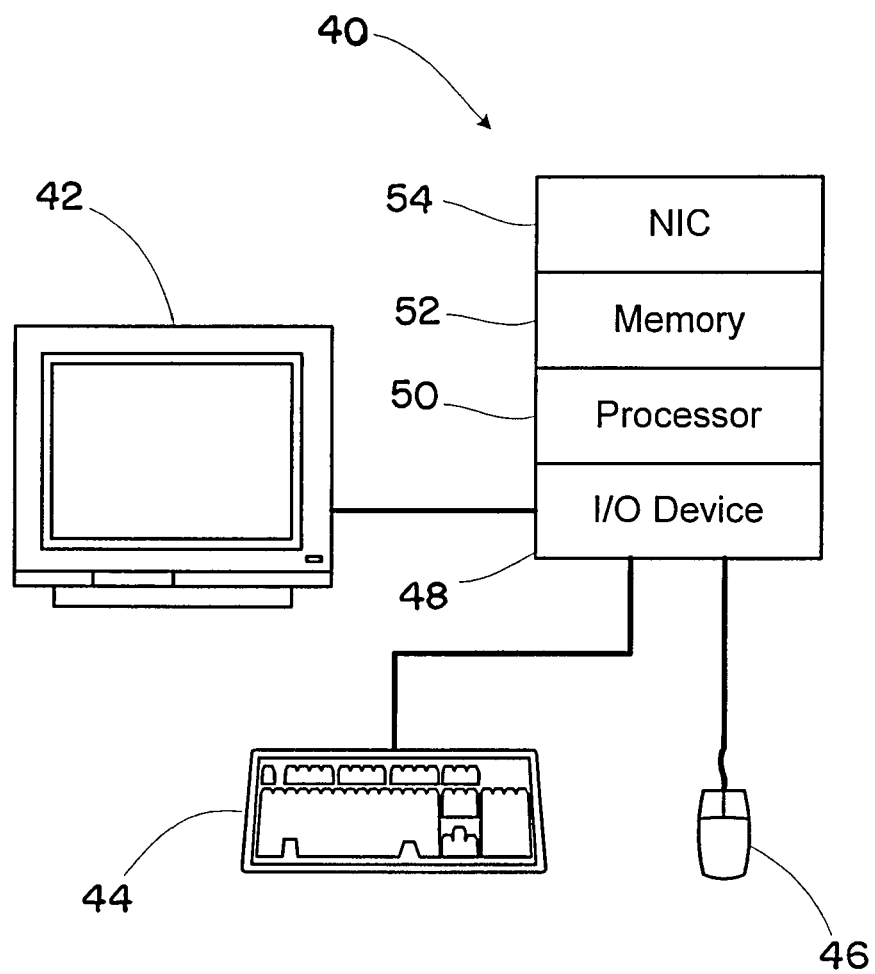
FIG. 5 is a block diagram of an exemplary computer system that may be used to carry out one or more of the methods described herein.

Moving now to FIG. 5 there is shown a block diagram of an exemplary computer 40 that may be used to implement one or more of the methods described herein. The computer 40 may be a standalone computer, or it may be part of a medical navigation system, for example. The computer 40 may include a display 42 for viewing system information, and a keyboard 44 and pointing device 46 for data entry, screen navigation, etc. A computer mouse or other device that points to or otherwise identifies a location, action, etc., e.g., by a point and click method or some other method, are examples of a pointing device 46. Alternatively, a touch screen (not shown) may be used in place of the keyboard 44 and pointing device 46. The display 42, keyboard 44 and mouse 46 communicate with a processor via an input/output device 48, such as a video card and/or serial port (e.g., a USB port or the like).

A processor 50, such as an AMD Athlon 64® processor or an Intel Pentium IV® processor, combined with a memory 52 execute programs to perform various functions, such as data entry, numerical calculations, screen display, system setup, etc. The memory 52 may comprise several devices, including volatile and non-volatile memory components. Accordingly, the memory 52 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 50 and the memory 52 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 54 allows the computer 40 to communicate with other devices.

A person having ordinary skill in the art of computer programming and applications of programming for computer systems would be able in view of the description provided herein to program a computer system 40 to operate and to carry out the functions described herein. Accordingly, details as to the specific programming code have been omitted for the sake of brevity. Also, while software in the memory 52 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A device for registering in a medical navigation system a position and/or orientation of a patient's pelvis, comprising:
   a pelvic registration frame;
   a plurality of positioning elements arranged on the pelvic registration frame, wherein each one of the positioning elements is laterally spaced apart from and laterally movable relative to another one of the positioning elements to enable placement of the positioning elements at defined pelvic points of the patient's pelvis; and
   at least one position transmitter arranged in an unambiguously defined position and/or orientation relative to the pelvic registration frame.

2. The device according to claim 1, wherein the at least one position transmitter is assigned to the frame of the device.

3. The device according to claim 1, wherein a spatial orientation of the pelvic registration frame and/or the defined position and/or orientation of the at least one position transmitter is assigned to one or more anatomical pelvic planes.

4. The device according to claim 1, wherein the at least one position transmitter is an electromagnetic sensor, and a position and/or orientation of the electromagnetic sensor is detectable by a medical tracking system.

5. The device according to claim 4, wherein the electromagnetic sensor is a magnetic tracking coil.

6. The device according to claim 4, wherein the at least one position transmitter is a plurality of position transmitters.

7. The device according to claim 4, wherein the electromagnetic sensor is attached to the frame in a fixed orientation.

8. The device according to claim 1, wherein the pelvic registration frame comprises at least one positioning and/or orientation aid for a sensor carrier, said sensor carrier bearing an electromagnetic sensor or magnetic tracking coil, wherein the at least one positioning and/or orientation aid arranges the sensor carrier so as be in a preset direction and/or position relative to the pelvic registration frame.

9. The device according to claim 8, wherein the at least one positioning and/or orientation aid is a recess.

10. The device according to claim 1, wherein the at least on position transmitter is a plurality of position transmitters designed as x-ray markers that consist of a material that is impermeable to x-ray radiation, said plurality of position transmitters arranged on the pelvic registration frame, and wherein at least in the vicinity of the x-ray markers the pelvic registration frame consists of a material that is permeable to x-ray radiation.

11. The device according to claim 10, wherein the x-ray markers are arranged on the pelvic registration frame as attachments or inserts.

12. The device according to claim 10, wherein the x-ray markers form or replace a part of the pelvic registration frame contour.

13. The device according to claim 12, wherein the part of the frame contour is an edge portion or corner portion of the pelvic registration frame.

14. The device according to claim 1, wherein the pelvic registration frame defines a plane that is parallel to a pelvic plane.

15. A method for registering in a medical navigation system a position and/or orientation of a patient's pelvis using a pelvic registration device including a) a pelvic registration frame, b) a plurality of positioning elements arranged on the pelvic registration frame, wherein each one of the positioning elements is laterally spaced apart from and laterally movable relative to another one of the positioning elements to enable placement of the positioning elements at defined pelvic points of the patient's pelvis, and c) at least one position transmitter arranged in an unambiguously defined position and/or orientation relative to the frame, said method comprising:

attaching a trackable device to the patient's pelvis;

placing each of said plurality of positioning elements on a corresponding pelvic point of the defined pelvic points;

obtaining x-ray images of the patient's pelvis and the pelvic registration device, and storing a location of the trackable device as the images are obtained;

determining a plane of the registration frame based on a detected position of the at least one position transmitter; and calculating the position and/or orientation of the patient's pelvis based on the determined plane relative to the trackable device.

* * * * *